United States Patent [19]

Lele

[11] Patent Number: 4,893,624

[45] Date of Patent: Jan. 16, 1990

[54] DIFFUSE FOCUS ULTRASOUND HYPERTHERMIA SYSTEM

[75] Inventor: Padmakar P. Lele, Winchester, Mass.

[73] Assignee: Massachusetts Institute of Technology, Cambridge, Mass.

[21] Appl. No.: 209,520

[22] Filed: Jun. 21, 1988

[51] Int. Cl.$^4$ .............................................. A61F 7/00
[52] U.S. Cl. .................................. 128/399; 128/24 A
[58] Field of Search ................ 128/399, 24 A, 660.03, 128/660.09, 661.01; 73/642, 618

[56] References Cited

U.S. PATENT DOCUMENTS

| | | | |
|---|---|---|---|
| 2,913,602 | 11/1959 | Joy ..................................... | 128/24 A |
| 3,237,623 | 3/1966 | Gordon ............................. | 128/24 A |
| 3,958,559 | 5/1976 | Glenn et al. ..................... | 128/663.01 |
| 4,207,901 | 6/1980 | Nigam ............................. | 128/663.01 |
| 4,397,314 | 8/1983 | Vaguine .............................. | 128/399 |
| 4,441,486 | 4/1984 | Pounds ............................. | 128/24 A |
| 4,549,533 | 10/1985 | Cain et al. ......................... | 128/24 A |
| 4,556,070 | 12/1985 | Vaguine et al. ..................... | 128/804 |
| 4,586,512 | 5/1986 | Do-huu et al. ...................... | 128/660 |
| 4,620,546 | 11/1986 | Aida et al. ......................... | 128/660 |
| 4,622,972 | 11/1986 | Giebeler, Jr. ....................... | 128/399 |
| 4,646,756 | 3/1987 | Watmough et al. ................. | 128/804 |
| 4,708,127 | 11/1987 | Abdelghani ....................... | 128/24 A |

FOREIGN PATENT DOCUMENTS 0214782 3/1987 European Pat. Off. .
3150513 6/1983 Fed. Rep. of Germany ...... 128/399

OTHER PUBLICATIONS

Fessenden et al., "Experience . . . Ultrasound . . . ", IEEE Trans. Biomed. Eng., BME-31, No. 1, Jan., 1984, pp. 126-135.

Lele, P. P., 1975, "Hyperthermia by Ultrasound", Proceedings of the International Symposium on Cancer Therapy by Hyperthermia and Radiation, American College of Radiology, Washington, D.C., pp. 168-178.

Lele, P. P., 1981, "An Annular-Focus Ultrasonic Lens for Production of Uniform Hyperthermia in Cancer Therapy", Ultrasound in Medicine and Biology, pp. 191-193.

Lele, P. P., 1983, "Physical Aspects and Clinical Studies with Ultrasonic Hyperthermia", Hyperthermia in Cancer Therapy, G. K. Hall and Co., pp. 333-367.

Sleefe, G. E. and Lele, P. P., 1985, "Phased Arrays for the Induction of Local Hyperthermia", Proceedings of the IEEE 1985 Ultrasonics Symposium.

Lele, P. P., 1986, "Rationale, Technique and Clinical Results with Scanned, Focused Ultrasound (SIMFU) System", IEEE Eighth Annual Conference of the Engineering in Medicine and Biology Society.

Lele, P. P., 1987, "Ultrasound: Synergistic Effects and Application in Cancer Therapy by Hyperthermia", Ultrasound, Plenum Publishing Corporation, pp. 307-332.

Lele, P. P., 1987, "Effects of Ultrasound on 'Solid' Mamalian Tissues and Tumors in Vivo", Ultrasound, Plenum Publishing Corporation, pp. 275-306.

Lele, P. P. and J. Goddard, 1987, "Optimizing Insonation Parameters in Therapy Planning for Deep Heating by SIMFU", IEEE Ninth Annual Conference of the Engineering in Medicine and Biology Society.

Lele, P. P., Goddard, J., Blanter, M., 1987, "Clinical Results with Scanned, Intensity-Modulated, Focused Ultrasound (SIMFU) System ", Proceedings of 73rd Annual Meeting, Radiological Society of North American, pp. 157-170.

Primary Examiner—Lee S. Cohen
Attorney, Agent, or Firm—Thomas J. Engellenner; David A. Jacobs

[57] ABSTRACT

A system for delivering ultrasound hyperthermic therapy to a subject includes a plurality of piezoelectric ultrasound transducer elements arranged in a two-dimensional array to provide multiple sources of ultrasonic energy, and variable activation elements for activating the transducer elements individually and at variable electrical energy levels. A plurality of lens elements is provided for transmitting the multiple sources of ultrasonic energy to the subject, in conjunction with focusing elements which individually vary the attitude of the lens elements to change the focal regions of the individual lenses. The transducer elements and lens elements can be corresponding "pie-slice" sectors arranged in a circular array, in combination with a central circular transducer and lens.

28 Claims, 2 Drawing Sheets

DIFFUSE FOCUS ULTRASOUND HYPERTHERMIA SYSTEM

The U.S. Government has rights in this invention pursuant to Contract Number CA 31303-03 awarded by the National Cancer Institute.

BACKGROUND OF THE INVENTION

This invention relates generally to systems for ultrasound hyperthermia, and, more particularly, relates to apparatus and methods for delivering ultrasonic energy in hyperthermic treatment of internal cancers and other diseases which respond to temperature elevation.

Production of a controllable level of temperature elevation or hyperthermia at pre-selected locations and volumes of tissue has been found to be of significant therapeutic value in the treatment of patients with cancer or other diseases. Several methods utilizing focused ultrasound to produce such hyperthermia have been described in the art. See, for example, the following publications:

Lele, P. P., 1975, "Hyperthermia by Ultrasound," Proceedings of the International Symposium on Cancer Therapy by Hyperthermia and Radiation, American College of Radiology, Washington, D.C., pp. 168–178;

Lele, P. P., 1981, "An Annular-Focus Ultrasonic Lens for Production of Uniform Hyperthermia in Cancer Therapy", Ultrasound in Medicine and Biology, pp. 191–193;

Lele, P. P., 1983, "Physical Aspects and Clinical Studies with Ultrasonic Hyperthermia," *Hyperthermia in Cancer Therapy*, G. K. Hall and Co., pp. 333–367;

Sleefe, G. E. and Lele, P. P., 1985, "Phased Arrays for the-induction of Local Hyperthermia," Proceedings of the IEEE 1985 Ultrasonics Symposium;

Lele, P. P., 1986, "Rationale, Technique and Clinical Results with Scanned, Focused Ultrasound (SIMFU) System," IEEE Eighth Annual Conference of the Engineering in Medicine and Biology Society;

Lele, P. P., 1987, "Ultrasound: Synergistic Effects and Application in Cancer Therapy by Hyperthermia," Plenum Publishing Corporation;

Lele, P. P., 1987, "Effects of Ultrasound on 'Solid' Mamalian Tissues and Tumors in Vivo," Plenum Publishing Corporation; and Lele, P. P. and J. Goddard, 1987, "Optimizing Insonation Parameters in Therapy Planning for Deep Heating by SIMFU," IEEE Ninth Annual Conference of the Engineering in Medicine and Biology Society.

Further, the following U.S. Patents disclose examples of recent developments in the hyperthermia field:

U.S. Pat. No. 4,441,486, Pounds
U.S. Pat. No. 4,549,533, Cain et al
U.S. Pat. No. 4,586,512, Do-huu et al
U.S. Pat. No. 4,622,972, Giebeler, Jr.

The Pounds patent discloses a hyperthermia system including a plurality of transducers mounted in an isopherical configuration. Each transducer is configured so that its compressional mode of vibration is suppressed near the center.

The Cain et al patent discloses ultrasound generating apparatus having a plurality of side-by-side tapered piezoelectric transducer elements. Means are provided for energizing the transducer elements with electrical energy having a frequency which is varied to modulate the ultrasound produced by the transducer elements.

The Do-huu et al patent discloses an emitter which focuses ultrasonic radiation into biological tissues for producing localized heating. The radiation emitter consists of a piezoelectric plate subdivided into annular radiating zones of equal width by a set of concentric circular grooves.

The Giebeler, Jr. patent discloses an ultrasound hyperthermia applicator comprising a plurality of transducers which can be operated in different grouping modes. The beams from these elements can be individually focused according to a spiral or multi-spiral focusing scheme, in an attempt to provide uniform heating, without scanning, of a volume greater than the inherent focal size of the individual transmitter elements.

Additionally, European patent application No. 214,782 of Umemura et al discloses a transducer composed of a plurality of elements divided at least in a circumferential direction. The phases of drive signals may be changed according to the respective positions of the oscillating elements, to form an annular focal zone having a variable radius.

Certain conventional hyperthermia systems, among those described above, utilize an "annular focus" lens for generating hyperthermia of limited tissue volumes, up to 3 centimeters in diameter. Where heating of larger tissues volumes is required, prior art systems utilize single-focus ultrasonic transducers mechanically driven through selected trajectories.

Conventional mechanically scanned ultrasound hyperthermia systems suffer from a number of deficiencies. In particular, mechanical scanning or translation of the transducers limits the scan speed attainable with such systems. Translation of the transducers also necessitates cumbersome methods, such as open-water baths, for coupling ultrasonic energy into the patient. These systems require considerable mechanical adjustment and calibration which complicate the therapeutic protocol. Further, to avoid potentially damaging high peak intensity levels, conventional hyperthermia devices deliver low ultrasound energy levels.

Accordingly, there exists a need for hyperthermia methods and apparatus which permit the delivery of high overall levels of ultrasonic energy while eliminating high peak intensities, and which provide high scan speed, facilitated coupling of ultrasonic energy, and simplified therapeutic protocol.

It is an object of the invention to provide improved ultrasound hyperthermia apparatus.

It is another object of the invention to provide ultrasound hyperthermia apparatus which delivers high overall levels of ultrasonic energy while eliminating high peak intensities.

It is a further object of the invention to provide ultrasound hyperthermia apparatus characterized by enhanced speed and reliable operation.

Other general and specific objects of the invention will in part be obvious and will in part appear hereinafter.

SUMMARY OF THE INVENTION

The foregoing objects are attained by the invention, which provides an ultrasonic hyperthermia system for delivering hyperthermic therapy to a subject. In accordance with one aspect of the invention, the system includes a plurality of piezoelectric transducer elements arranged in a two-dimensional array to provide multiple sources of ultrasonic energy.

The invention also includes variable activation elements for activating the transducer elements individually and at variable electrical energy levels. This individual, variable activation permits the multiple sources of ultrasonic energy to vary in intensity.

The invention further includes a plurality of lens elements for transmitting the multiple sources of ultrasonic energy to the subject, and focusing elements for varying the position of the lens elements individually to permit variations in the focal regions of the multiple sources of ultrasonic energy.

In one aspect of the invention, the transducer elements are arranged in a circular array. In a further aspect of the invention, the elements are pie-shaped elements. The invention also includes pie-shaped lens elements disposed between the transducer elements and the subject.

In another aspect of the invention, the focusing elements further include tilting elements for tilting the individual lens elements to change their focal regions. In particular, the tilting elements modulate the attitude of the individual lens elements to change the focal shape and depth of the individual lens elements.

The invention accordingly comprises apparatus embodying features of construction, combinations of elements and arrangements of parts, as exemplified in the following detailed disclosure.

BRIEF DESCRIPTION OF THE DRAWINGS

For a more thorough understanding of the nature and objects of the invention, reference should be made to the following detailed description and the accompanying drawings, in which.

DESCRIPTION OF PREFERRED EMBODIMENTS

Figure 1:
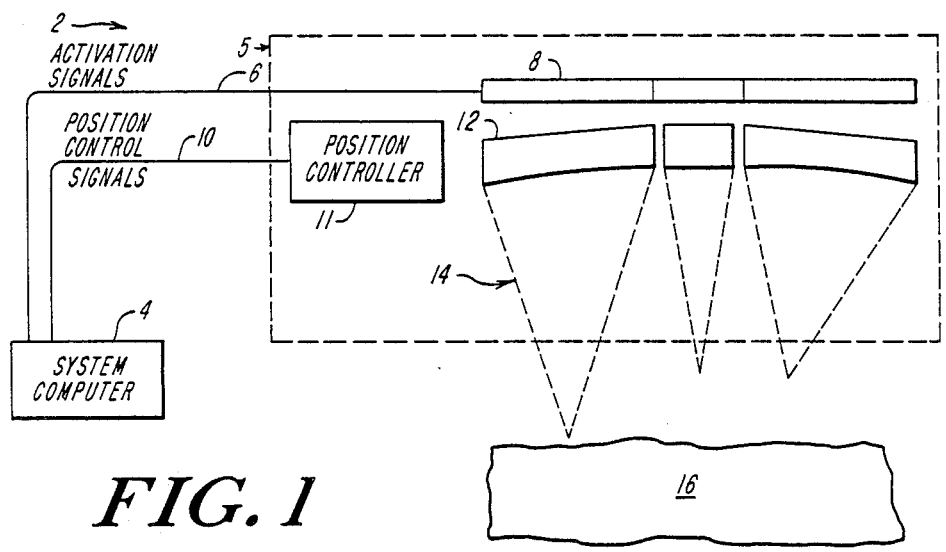
FIG. 1 is a schematic diagram depicting a diffuse-focus ultrasound hyperthermia system according to the invention.

In FIG. 1 a diffuse-focus, ultrasound hyperthermia system according to the invention is shown. The illustrated hyperthermia system 2 includes a system computer 4 and an ultrasound generation module 5, for generating a diffuse-focus beam 14 and directing the beam 14 into target volume 16. Those skilled in the art will appreciate that mechanical controls, such as potentiometers, can be substituted for system computer 4.

As FIG. 1 illustrates, system computer 4 generates activation signals 6. These signals are transmitted to transducer array 8 contained in diffuse-focus ultrasound generation module 5. The respective elements of transducer array 8 respond to the activation signals in a manner known in the art, to generate ultrasonic energy. In a preferred embodiment of the invention, each element of transducer array 8 receives independent activation signals.

System computer 4 also generates position control signals 10, which are transmitted to position controller elements 11 coupled to respective lens elements of lens array 12. The position controller elements 11 are preferably conventional servo or stepper motors. In response to the position signals 10, the position controllers 11 vary the inclination, or "tilt" of respective lens elements of lens array 12 to change focal characteristics of lens array 12. In particular, modulating the inclination of respective lens elements of lens array 12 provides control of the focal shape of beam 14 in target volume 16, as discussed in greater detail below in connection with FIG. 3.

The illustrated hyperthermia system 2 eliminates translation of the transducer array 8 and the need for the open water-bath energy coupling media typically utilized in connection with conventional mechanically-scanned ultrasound hyperthermia systems. Hyperthermia is produced by activating the multi-element transducer array 8, which is capable of both focusing and scanning of the ultrasonic beam field 14.

Figure 2:
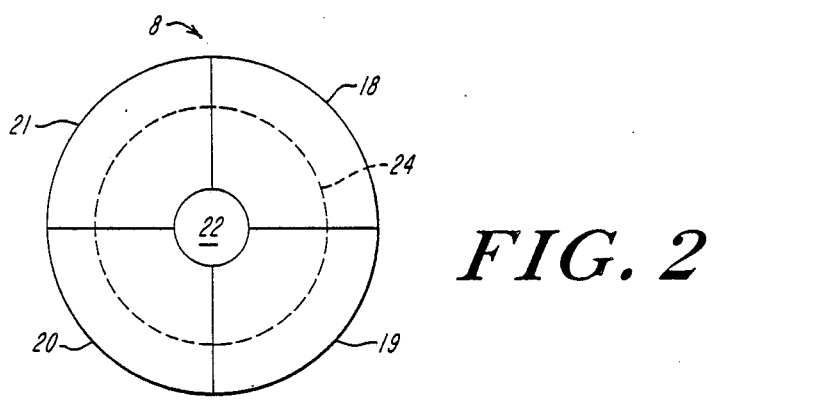
FIG. 2 is a plan view of transducer elements utilized in connection with the system of FIG. 1.

FIG. 2 depicts a preferred configuration of transducer elements utilized in connection with the embodiment of FIG. 1. The illustrated transducer array 8 is preferably a circular ceramic piezoelectric disk, which may, for example, be 20 centimeters in diameter, and which is segmented into equal-sized "pie-slice" sectors 18–21. The transducer array 8 can also have an additional circular center region 22.

Figure 3:
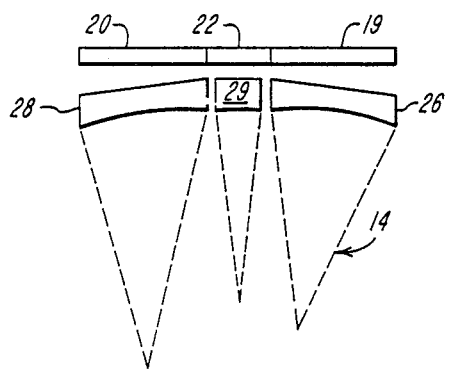
FIG. 3 is a sectional view giving detail of transducer elements and lens elements utilized in connection with the system of FIG. 1.

As illustrated in FIG. 3, in front of each of the transducer sector elements 18–21 is positioned an arc of an annular focus lens. Thus, for example, annular focus lens element 28 is positioned in front of transducer element 20, and annular focus lens element 26 is positioned in front of transducer element 19. Additionally, either a spherical or an annular-focus lens is positioned to focus the output of the central transducer section 22. A spherical lens element 29 is positioned in front of central transducer section 22 in the illustrated embodiment.

Each of the sector lenses, including illustrated lenses 26, 28 and 29, are preferably mounted on conventional multiple-degree-of-freedom mounts so that the lenses can be tilted manually, mechanically, electro-mechanically, or by driving a wedge of ultrasound transmitting medium between the respective lens and its corresponding transducer element. For example, position control elements utilizing servo or stepper motors can be employed for varying the position of the lens elements, responsive to position control signals generated by a system computer 4 in a manner known in the art. The resulting heating patterns produced are variable-diameter circular annuli or quasi-elliptical annuli. Circular region 24, indicated by dashed lines in FIG. 2, denotes one such heating pattern. Thus, the shape of the heating pattern is a function of lens attitude, while the depth of heating is largely a function of frequency. In practice, pattern shape is generally more critical than pattern depth.

The illustrated embodiment of the invention can advantageously produce stationary, non-circular patterns which conform to tumor shape. Alternatively, heating patterns can be changed during the hyperthermia process. Another important advantage of the invention is the elimination of high peak intensities which can cause tissue destruction. Additionally, the invention permits heating at the margin areas of tumors, where tumor growth occurs.

In a further preferred embodiment of the invention, the position controller 11, in cooperation with system computer 4, can introduce a substantially randomized time-based perturbation in the tilt of the individual lens elements. This perturbation, or "wobble," equalizes the thermal dose delivered to the target to prevent localized hot spots, thus further reducing the possibility of cavitation or other mechanisms of tissue damage.

Additionally, the invention can be practiced in an embodiment utilizing multiple diffuse-focus ultrasound generation modules, arranging in a circular pattern about a center of heating. In this embodiment, system computer 4 modulates the power generated by the individual elements of the transducer array 8, to provide apodization, i.e. amplitude shading. In particular, greater power is generated by transducer elements at the periphery of the circle, to avoid overheating the center of the target area. This preferred apodization or amplitude shading, practiced in connection with a multiple target configuration, is depicted in FIG. 5.

Figure 4:
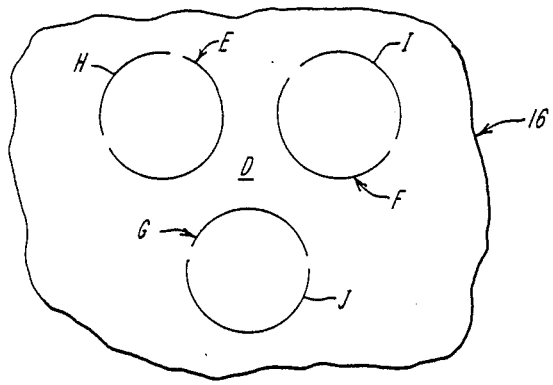
FIG. 4 depicts apodization or amplitude shading of a multiple target area configuration in accordance with another embodiment of the invention.

FIG. 4 shows exemplary target areas A, B, C in a target tissue 16. Each area A, B, C is heated by a respective ultrasound module, bounded by substantially circular or elliptical boundary E, F, G, respectively, and arranged in a circular pattern around a center D of applied energy. Apodization is implemented by applying higher energy levels to regions H, I, J (i.e. the regions most distant from center D) than to other regions of target areas A, B, C, respectively.

Figure 5:
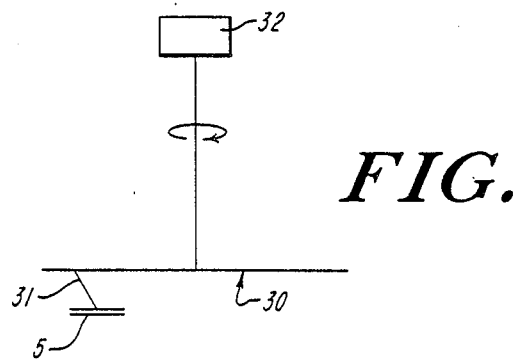
FIG. 5 depicts a further embodiment of a diffuse-focus ultrasound hyperthermia system according to the invention, utilizing a rotating index table.

In yet another embodiment of the invention, depicted in FIG. 5, a diffuse-focus ultrasound generation module 5 can be connected by a conventional multiple-degree-of-freedom coupling 31 to the periphery of a rotating index table 30, and the index table 30 rotated by stepper motor 32, to provide multiple angles of attack from a single ultrasound generation module 5. A dynamic, synchronized amplitude shading algorithm is preferably utilized in connection with this embodiment of the invention, for maintaining higher energy levels at the periphery of the heating area, and lower energy levels at the center. Alternatively, multiple transducers, employing different frequencies and focal depths, can be utilized in connection with a rotating index table. It will also be appreciated that while the invention obviates the need for scanning or translating of the transducers, the invention can be practiced in an embodiment utilizing multiple transducer arrays and conventional X-Y scanning mechanisms.

Those skilled in the art will appreciate that power modulation and modulation of beam scanning can be performed, to permit heating of both deep and irregularly shaped tumors. Moreover, it will be understood that while the illustrated transducer/lens configuration produces a variable-diameter, variable-depth ultrasonic beam field 14, other configurations, which may utilize more sectors, or a mosaic of separate transducers, may be employed and are within the scope of the invention. A further example of a useful transducer/lens configuration is illustrated in FIG. 6.

Figure 6:
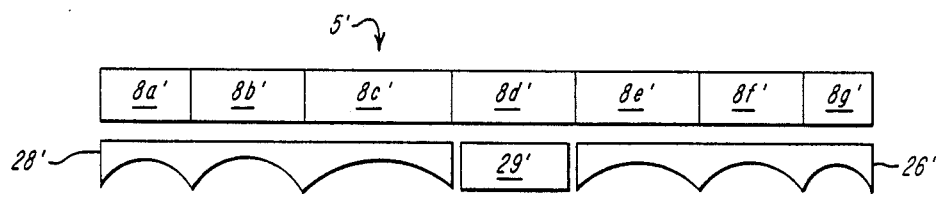
FIG. 6 is a sectional view giving detail of transducer elements and lens elements utilized in connection with another embodiment of the invention.

In particular, as FIG. 6 illustrates, as the radius of the target area increases, it is useful to increase the number of lens elements, to provide an ultrasonic beam field of larger diameter. Accordingly, in comparison with the embodiment illustrated in FIG. 3, the diffuse-focus ultrasound generation module 5' illustrated in FIG. 6 includes a transducer array 8' having an increased number of transducer sector elements $8a'-8g'$. Positioned in front of each of the transducer sector elements $8a'-8g'$ is a respective arc of annular focus lenses 26' and 28'. Each of lenses 26' and 28' has a correspondingly increased number of focusing arcs. Additionally, a spherical lens element 29' is positioned in front of central transducer segment $8d'$.

It will thus be seen that the invention efficiently attains the objects set forth above, among those made apparent from the preceding description. In particular, the invention provides a diffuse-focus ultrasonic hyperthermia system capable of heating both deep and irregularly shaped tumors, while requiring no mechanical translation of the transducer head.

It will be understood that various additions, subtractions and other modifications can be made in the above construction and in the foregoing sequences of operation without departing from the scope of the invention. For example, the invention can be practiced in an embodiment utilizing multiple diffuse-focus ultrasound generation modules 5 like that depicted in FIG. 1, in combination with a conventional X-Y scanning mechanism. It is accordingly intended that all matter contained in the above description or shown in the accompanying drawings be interpreted as illustrative rather than in a limiting sense.

It is also to be understood that the following claims are intended to cover all of the generic and specific features of the invention as described herein, and all statements of the scope of the invention which, as a matter of language, might be said to fall therebetween.

Having described the invention, what is claimed as new and secured by Letters Patent is:

1. An ultrasonic hyperthermia system for delivering hyperthermic therapy to a subject, the system comprising:
    a plurality of piezoelectric transducer elements arranged in a two-dimensional array to provide multiple sources of ultrasonic energy;
    variable activation means for activating the transducer elements individually and at variable electrical energy levels to permit the multiple sources of ultrasonic energy to vary in intensity;
    a further plurality of lens elements, coupled to the plurality of transducer elements, to transmit the multiple sources of ultrasonic energy to the subject as a diffuse-focus beam having a selected dimension in a direction substantially perpendicular to a direction of propagation; and
    focusing means for dynamically varying the position of the lens elements individually to permit variations in the focal regions of the multiple sources of ultrasonic energy, said variations in focal regions including variations in the selected dimension of the diffuse-focus beam.

2. The system of claim 1 wherein the transducer elements are arranged in a circular array.

3. The system of claim 2 wherein the transducer elements are pie-shaped elements.

4. The system of claim 3 wherein the plurality of lens elements includes pie-shaped lens elements adopted to be disposed between the transducer elements and the subject.

5. The system of claim 1 wherein the focusing means further includes tilting means for tilting the individual lens elements to change their focal regions.

6. The system of claim 5 wherein the tilting means includes means for tilting the individual lens elements to change the focal depth of the individual lens elements.

7. The system of claim 1, further including rotating means, supportingly connected to the array of transducer elements, for rotating the array of transducer elements through a selected orbital path.

8. An ultrasonic hyperthermia system for delivering hyperthermic therapy to a subject, the system comprising:
   a plurality of piezoelectric transducer elements arranged in a two-dimensional array to provide multiple sources of ultrasonic energy;
   variable activation means for activating the transducer elements individually and at variable electrical energy levels to permit the multiple sources of ultrasonic energy to vary in intensity;
   a further plurality of lens elements, coupled to the plurality of transducer elements, to transmit the multiple sources of ultrasonic energy to the subject; and
   focusing means for varying the position of the lens elements individually to permit variations in the focal regions of the multiple sources of ultrasonic energy, the focusing means including tilting means for tilting the individual lens elements to change their focal regions, the tilting means including (i) means for tilting the individual lens elements to change the focal depth of the individual lens elements, and (ii) means for introducing a substantially randomized perturbation in the tilt of the individual lens elements.

9. An ultrasonic hyperthermia system for delivering hyperthermic therapy to a subject, the system comprising:
   a plurality of piezoelectric transducer elements arranged in a two-dimensional array to provide multiple sources of ultrasonic energy;
   variable activation means for activating the transducer elements individually and at variable electrical energy levels to permit the multiple sources of ultrasonic energy to vary in intensity;
   a further plurality of lens elements to transmit the multiple sources of ultrasonic energy to the subject; and
   focusing means for varying the position of the lens elements individually to permit variations in the focal regions of the multiple sources of ultrasonic energy, the focusing means including wedge focusing means for selectively positioning a wedge of ultrasound transmitting medium between an individual lens element and a corresponding transducer element.

10. An ultrasonic hyperthermia system for delivering hyperthermic therapy to a subject, the system comprising:
    a plurality of ultrasonic energy generating modules, each module including
    (i) a plurality of piezoelectric transducer elements arranged in a two-dimensional array to provide multiple sources of ultrasonic energy;
    (ii) variable activation means for activating the transducer elements individually and at variable electrical energy levels to permit the multiple sources of ultrasonic energy to vary in intensity;
    (iii) a further plurality of lens elements, coupled to the plurality of transducer elements, to transmit the multiple sources of ultrasonic energy to the subject; and
    (iv) focusing means for varying the position of the lens elements individually to permit variations in the focal regions of the multiple sources of ultrasonic energy.

11. The system of claim 10, further including scanning means, supportingly connected to said ultrasonic energy generating modules, for scanning said ultrasound generating modules across a selected area.

12. The system of claim 10, further including amplitude shading means for selectively varying, in accordance with a selected geometric pattern, the amplitude of ultrasonic energy generated by individual transducer elements.

13. The system of claim 10, further including rotating means, supportingly connected to said ultrasonic energy generating modules, for rotating the ultrasonic energy generating modules through a selected orbital path.

14. An ultrasonic hyperthermia system for delivering hyperthermic therapy to a subject, the system comprising:
    a plurality of piezoelectric transducer elements arranged in a two-dimensional array to provide multiple sources of ultrasonic energy;
    variable activation means for activating the transducer elements individually and at variable electrical energy levels to permit the multiple sources of ultrasonic energy to vary in intensity;
    a further plurality of lens elements to transmit the multiple sources of ultrasonic energy to the subject;
    focusing means for varying the position of the lens elements individually to permit variations in the focal regions of the multiple sources of ultrasonic energy;
    rotating means, supportingly connected to the array of transducer elements, for rotating the array of transducer elements through a selected orbital path; and
    amplitude shading means, responsive to the instantaneous angular position of the array of transducer elements, for selectively varying the amplitude of ultrasonic energy generated by individual transducer elements.

15. A method for delivering hyperthermic therapy to a subject, the method comprising the steps of:
    arranging a plurality of piezoelectric transducer elements in a two-dimensional array to provide multiple sources of ultrasonic energy;
    activating the transducer elements individually and at variable electrical energy levels to permit the multiple sources of ultrasonic energy to vary in intensity;
    positioning a further plurality of lens elements to transmit the multiple sources of ultrasonic energy to the subject as a diffuse-focus beam having a selected dimension in a direction substantially perpendicular to a direction of propagation; and
    varying the position of the lens elements individually to permit variations in the focal regions of the multiple sources of ultrasonic energy, said variations in focal regions including variations in the selected dimension of the diffuse-focus beam.

16. The method of claim 15 wherein the step of arranging the plurality of piezoelectric transducer elements includes the step of arranging the transducer elements in a circular array.

17. The method of claim 15 further comprising the step of configuring the transducer elements as pie-shaped transducer elements.

18. The method of claim 17, further comprising the step of configuring the lens elements as pie-shaped lens elements disposed between the transducer elements and the subject.

19. The method of claim 15 wherein the step of varying the position of the lens elements includes the step of tilting the individual lens elements to change their focal regions.

20. The method of claim 19 wherein the step of varying the position of the lens elements includes the step of tilting the individual lens elements to change the focal depth of the individual lens elements.

21. The method of claim 15, further including the step of rotating the array of transducer elements through a selected orbital path.

22. A method for delivering hyperthermic therapy to a subject, the method comprising the steps of:
arranging a plurality of piezoelectric transducer elements in a two-dimensional array to provide multiple sources of ultrasonic energy;
activating the transducer elements individually and at variable electrical energy levels to permit the multiple sources of ultrasonic energy to vary in intensity;
positioning a further plurality of lens elements to transmit the multiple sources of ultrasonic energy to the subject; and
varying the position of the lens elements individually to permit variations in the focal regions of the multiple sources of ultrasonic energy, wherein the step of varying the position of the lens elements including the step of tilting the individual lens elements to change their focal regions, and the step of tilting the individual lens elements includes the step of introducing a substantially randomized perturbation in the tilt of the individual lens elements.

23. A method for delivering hyperthermic therapy to a subject, the method comprising the steps of:
arranging a plurality of piezoelectric transducer elements in a two-dimensional array to provide multiple sources of ultrasonic energy;
activating the transducer elements individually and at variable electrical energy levels to permit the multiple sources of ultrasonic energy to vary in intensity;
positioning a further plurality of lens elements to transmit the multiple sources of ultrasonic energy to the subject; and
varying the position of the lens elements individually to permit variations in the focal regions of the multiple sources of ultrasonic energy, wherein the step of varying the position of the lens elements includes the step of selectively positioning a wedge of ultrasound transmitting medium between an individual lens element and a corresponding transducer element.

24. An ultrasonic hyperthermia method for delivering hyperthermic therapy to a subject, the method comprising the steps of:
arranging a plurality of piezoelectric transducer elements in a plurality of two-dimensional arrays to provide multiple sources of ultrasonic energy;
activating the transducer elements individually and at variable electrical energy levels to permit the multiple sources of ultrasonic energy to vary in intensity;
configuring a further plurality of lens elements to transmit the multiple sources of ultrasonic energy to the subject;
varying the position of the lens elements individually to permit variations in the focal regions of the multiple sources of ultrasonic energy; and
configuring the plurality of arrays as a plurality of ultrasonic energy generating modules.

25. The method of claim 24, further including the step of scanning the ultrasound generating modules across a selected area.

26. The method of claim 24, further including the step of selectively varying, in accordance with a selected geometric pattern, the amplitude of ultrasonic energy generated by individual transducer elements.

27. The method of claim 24, further including the step of rotating the ultrasonic energy generating modules through a selected orbital path.

28. A method for delivering hyperthermic therapy to a subject, the method comprising the steps of:
arranging a plurality of piezoelectric transducer elements in a two-dimensional array to provide multiple sources of ultrasonic energy;
activating the transducer elements individually and at variable electrical energy levels to permit the multiple sources of ultrasonic energy to vary in intensity;
positioning a further plurality of lens elements to transmit the multiple sources of ultrasonic energy to the subject;
varying the position of the lens elements individually to permit variations in the focal regions of the multiple sources of ultrasonic energy;
rotating the array of transducer elements through a selected orbital path;
responding to the instantaneous angular position of the array of transducer elements; and
selectively varying the amplitude of ultrasonic energy generated by individual transducer elements, responsive to the instantaneous angular position of the array of transducer elements.

* * * * *